United States Patent
Nitenson

(10) Patent No.: US 6,593,509 B1
(45) Date of Patent: Jul. 15, 2003

(54) ABSORBENT ARTICLE

(76) Inventor: Edward Nitenson, 653B Greenway Monor Dr., Florissant, MO (US) 63031

(*) Notice: Subject to any disclaimer, the term of this patent is extended or adjusted under 35 U.S.C. 154(b) by 127 days.

(21) Appl. No.: 09/699,576

(22) Filed: Oct. 31, 2000

Related U.S. Application Data

(60) Provisional application No. 60/177,536, filed on Jan. 21, 2000.

(51) Int. Cl.[7] .................................................. A61F 13/15

(52) U.S. Cl. ............. 604/358; 604/385.01; 604/385.14; 604/386

(58) Field of Search ............................ 2/311–322, 338; 604/317–402

(56) References Cited

U.S. PATENT DOCUMENTS

| | | | | |
|---|---|---|---|---|
| 4,723,952 A | * | 2/1988 | Esposito ..................... | 604/338 |
| 4,941,210 A | * | 7/1990 | Konucik ........................ | 2/171 |
| 5,013,307 A | * | 5/1991 | Broida ......................... | 604/338 |
| 5,035,523 A | * | 7/1991 | Allinder ........................ | 401/6 |
| 5,094,234 A | * | 3/1992 | Searcy ......................... | 602/68 |
| 6,139,515 A | * | 10/2000 | Ito .............................. | 602/67 |
| 6,308,342 B1 | * | 10/2001 | Qi ................................ | 2/403 |

* cited by examiner

Primary Examiner—Jeanette Chapman
(74) Attorney, Agent, or Firm—Henry W. Cummings

(57) ABSTRACT

In FIG. 1 a somewhat obese torso of a male is shown with the absorbent article 10 of the present invention applied to the groin area of the body. The Article includes a pad 12 and an elasticized adjustable belt 14 releasably attached to the ends 16 and 18 of the pad by alligator-type clips 20, or other suitable clips. The pad as shown in FIGS. 2 and 3 may have a narrowed central portion 22 approximately 1 inch wide, that is particularly convenient and comfortable when the article is used to absorb moisture such as perspiration in the groin area and inner thighs as illustrated in FIG. 1.

In FIGS. 4 and 4A another embodiment of absorbent article is shown that may be of the same configuration and made of any of the materials suggested for the pad of FIGS. 2 and 3, but preferably is of uniform width, that is, without the reduced mid-section 22. In FIGS. 4 and 4A and the pad 44 is shown positioned in the stomach crease 40 of an obese person (either male or female) and held in place by an elasticized belt 42 that may be identical to the belt 14 of FIG. 1. In this embodiment, the pad 44 is shown folded longitudinally along its center line so as to effectively provide two layers, one against each side of the crease 40. In the morbidly obese the stomach hangs down over the pelvic area, the pad is in an unfolded form with a side edge of the pad disposed at the innermost section of the crease.

In the embodiment of FIGS. 5–7, the pad 60 is shown formed with a longitudinally extending narrowed portion 62. The longitudinal area of reduced thickness is particularly desirable when the pad is to be used in the folded form as shown in FIG. 7.

In FIG. 8 yet another alternative construction of pad is shown. In this embodiment, the pad 70 is composed of two foam layers 72 and 74 or any of the other absorbent materials suggested above, separated by a central layer 76 that may be made of a cotton fabric or any other suitable material.

7 Claims, 5 Drawing Sheets

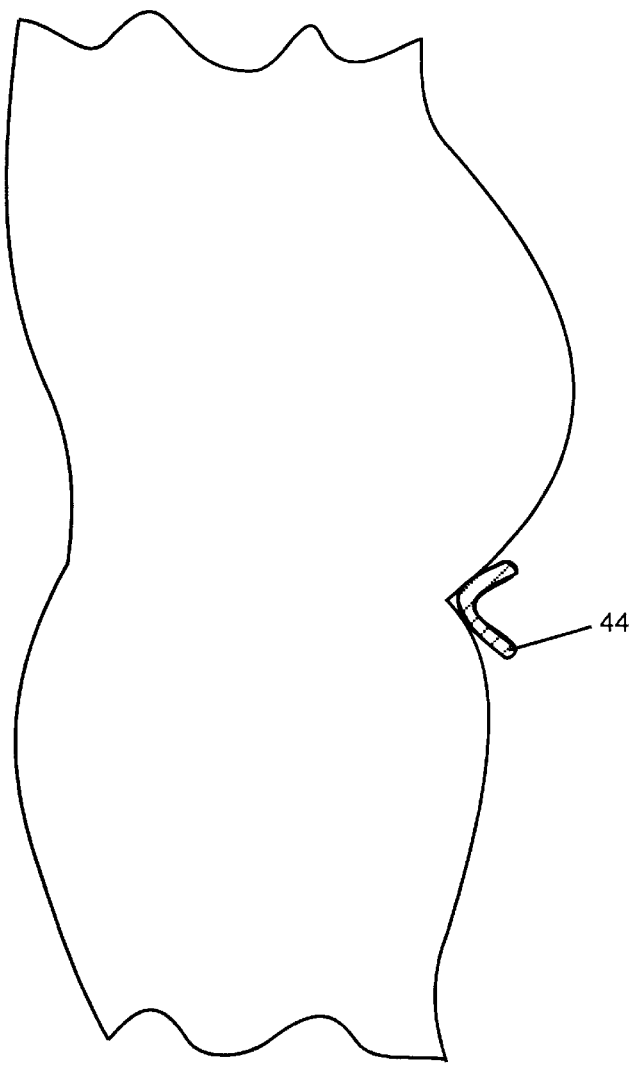
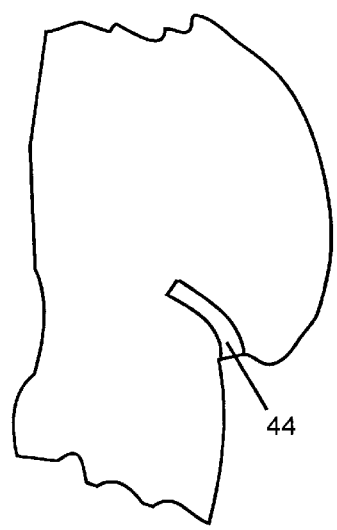
Fig. 4A
Fig. 4B

ABSORBENT ARTICLE

REFERENCE TO RELATED APPLICATION

This application is a continuation-in-part of application Ser. No. 60/177,536, filed Jan. 21, 2000.

FIELD OF THE INVENTION

This invention relates to absorbent articles for absorbing and retaining perspiration and other exuded body fluids. More particularly the articles are intended for use by obese people to absorb fluids in the stomach crease and for abese males to absorb perspiration on the scrotum and inner thighs. The articles also have application for male athletes.

SUMMARY OF THE INVENTION

A. Objects

One object of the present invention is to provide an article for absorbing and retaining perspiration and other exuded body fluids.

Another object of the invention is to provide an article for use by obese males to absorb perspiration on the scrotum and inner thighs, including male athletes.

SUMMARY

In FIG. 1 a somewhat obese torso of a male is shown with the absorbent article 10 of the present invention applied to the groin area of the body. The Article includes a pad 12 and an elasticized adjustable belt 14 releasably attached to the ends 16 and 18 of the pad by alligator-type clips 20, or other suitable clips. The pad as shown in FIGS. 2 and 3 may have a narrowed central portion 22 approximately 1 inch wide, that is particularly convenient and comfortable when the article is used to absorb moisture such as perspiration in the groin area and inner thighs as illustrated in FIG. 1.

In FIGS. 4 and 4A another embodiment of absorbent article is shown that may be of the same configuration and made of any of the materials suggested for the pad of FIGS. 2 and 3, but preferably is of uniform width, that is, without the reduced mid-section 22. In FIGS. 4 and 4A and the pad 44 is shown positioned in the stomach crease 40 of an obese person (either male or female) and held in place by an elasticized belt 42 that may be identical to the belt 14 of FIG. 1. In this embodiment, the pad 44 is shown folded longitudinally along its center line so as to effectively provide two layers, one against each side of the crease 40. In the morbidly obese the stomach hangs down over the pelvic area, the pad is in an unfolded form with a side edge of the pad disposed at the innermost section of the crease.

In the embodiment of FIGS. 5–7, the pad 60 is shown formed with a longitudinally extending narrowed portion 62. The longitudinal area of reduced thickness is particularly desirable when the pad is to be used in the folded form as shown in FIG. 7.

In FIG. 8 yet another alternative construction of pad is shown. In this embodiment, the pad 70 is composed of two foam layers 72 and 74 or any of the other absorbent materials suggested above, separated by a central layer 76 that may be made of a cotton fabric or any other suitable material.

In FIG. 9 another embodiment is illustrated, particularly suitable for use by obese people to absorb moisture in and adjacent the stomach crease. In this embodiment, the pad 90 whether made of a single ply of absorbent material or a multiple ply arrangement as shown in FIG. 8, is wider at its mid portion 92 than at its ends 94, as tapering smoothly in a gentle S-curve as shown. The wider mid portion 92 will fit into the deeper portion of the body crease beneath the stomach.

In another embodiment shown in FIGS. 10 and 11, an absorbent article100 includes a body portion 102 having a slit 104 approximately five to eight inches long to allow fitting the pad along the stomach and place the opened section under the scrotum to allow the pad to collect sweat. Alligator clips 120, 122 are used to connect the absorbent article 100 to a belt 114 having a buckle 116.

BRIEF DESCRIPTION OF THE DRAWINGS

FIG. 4A is a diagrammatic view of the side of the torso shown in FIG. 4 and further showing in section the pad that forms part of the absorbent article;

FIG. 4B is a view similar to FIG. 4A but showing the article used in a different configuration particularly suited for a morbidly obese person;

DETAILED DESCRIPTION

Figure 1:
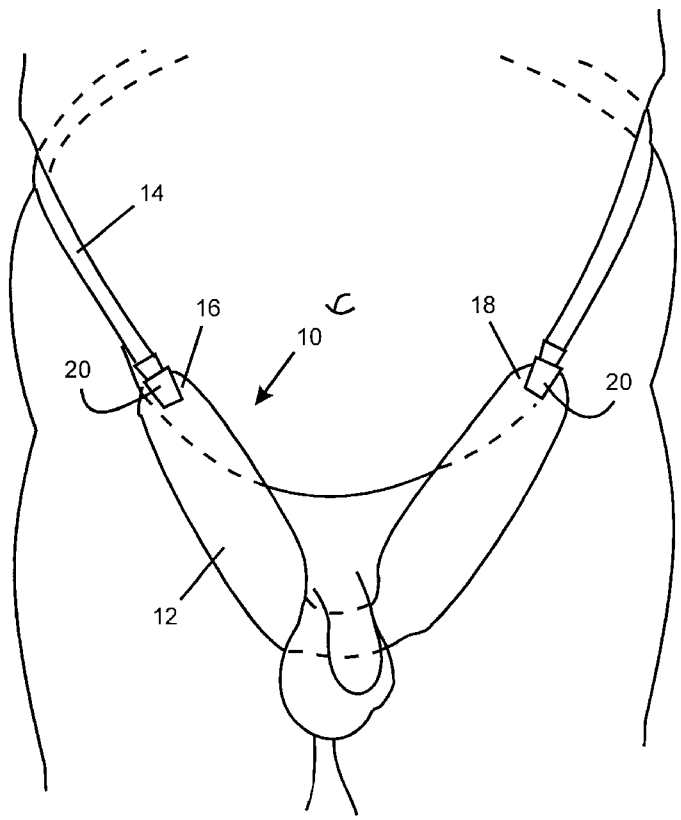
FIG. 1 is a front view of a male torso showing one embodiment of an absorbent article constructed in accordance with the present invention and applied to the scrotum area.

In FIG. 1 a somewhat obese torso of a male is shown with the absorbent article 10 of the present invention applied to the groin area of the body. The article includes a pad 12 and an elasticized adjustable belt 14 releasably attached to the ends 16 and 18 of the pad by alligator-type clips 20. While in the embodiment of FIGS. 2 and 3, the pad is shown made of foam material, it may be made of other soft and flexible absorbent materials such as cellulose, wood fluff, coform, meltblown or carded material, sphagnum moss or other conventional and commonly used materials presently used in diapers, feminine pads, panty liners, incontinent garments, underarm shields, bed pads, etc. The pad shown in FIG. 2 and may have a narrowed central portion 22 approximately 1 inch wide, that is particularly convenient and comfortable when the article is used to absorb moisture such as perspiration in the groin area and inner thighs as illustrated in FIG. 1. In this embodiment, both the top and bottom surfaces 24 and 26 are highly absorbent. When the article is worn as shown in FIG. 1, the narrower mid-section 22 of the pad extends behind the scrotum and over the inner thighs and may extend comfortably up to the bottom of the stomach (distended as shown) of the wearer.

Figure 2:
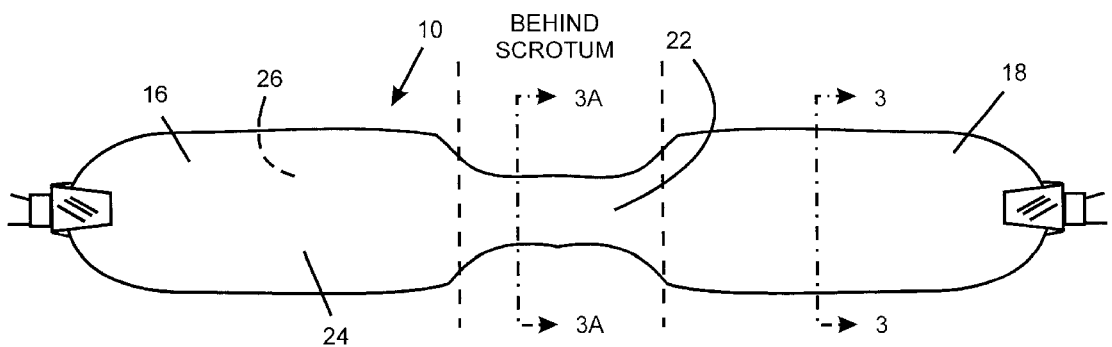
FIG. 2 is a plan view of the pad and ends of the elastic belt that comprises the article shown in FIG. 1.
Figure 3:
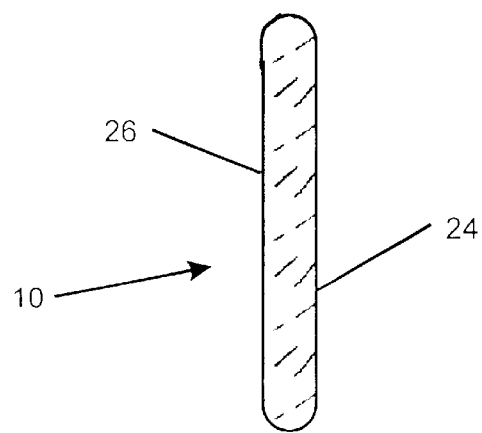
FIGS. 3 and 3A are cross sectional views of the pad forming part of the absorbent article, taken along section lines 3—3 and 3A—3A in FIG. 2.
Figure 3A:
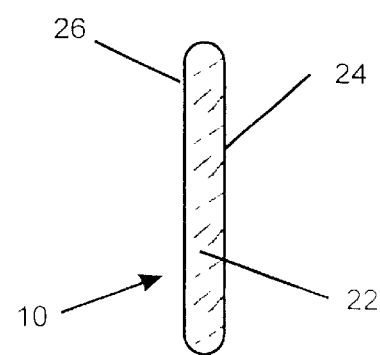
Figure 4:
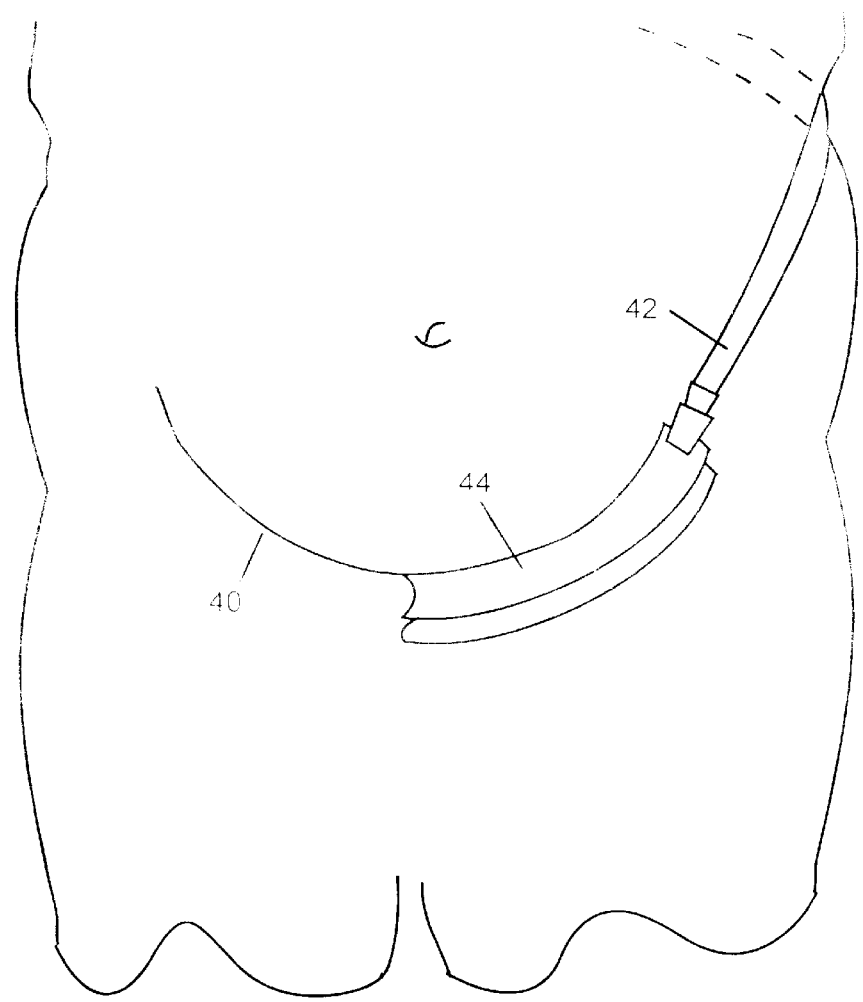
FIG. 4 is a front elevation view of a torso of an obese person showing another embodiment of the absorbent article constructed in accordance with the present invention and applied to the stomach crease.

In FIGS. 4 and 4A another embodiment of absorbent article is shown that may be of the same configuration and made of any of the materials suggested for the pad of FIGS. 2 and 3, but preferably is of uniform width, that is, may be without the reduced mid-section 22. In FIGS. 4 and 4A the pad 44 is shown positioned in the stomach crease 40 of an obese person (either male or female) and held in place by an elasticized belt 42 that may be identical to the belt 14 of FIG. 1. Preferably the length of this belt is adjustable. In this embodiment, the pad 44 is shown folded longitudinally along its center line so as to effectively provide two layers, one against each side of the crease 40. It may be more comfortable for the wearer, particularly if he/she is morbidly obese so that the stomach hangs down over the pelvic area, to use the pad in an unfolded form with a side edge of the pad disposed at the innermost section of the crease.

Figure 5:
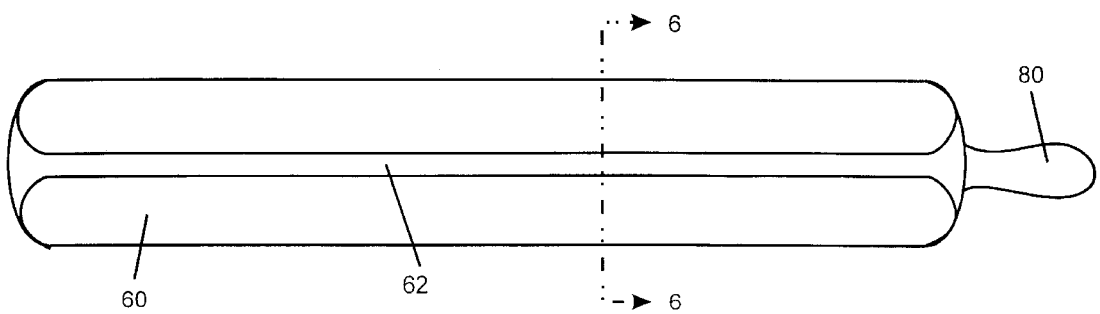
FIG. 5 is a plan view of another embodiment of the pad constructed in accordance with the present invention.
Figure 6:
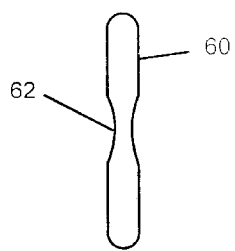
FIG. 6 is a cross sectional view of the pad taken along the section line 6—6 in FIG. 5.
Figure 7:
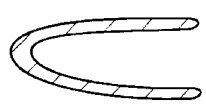
FIG. 7 is a cross sectional view of the pad shown in FIGS. 5 and 6, folded along the longitudinal center line as it may be used in the stomach crease of an obese person as suggested in FIGS. 4 and 4A.

In the embodiment of FIGS. 5–7, the pad 60 is shown formed with a longitudinally extending narrowed portion 62. In this configuration the pad may be made of a foam material as described in connection with FIG. 1 or of other absorbent materials including the well-known material suggested in connection with the first embodiment. The longitudinal area of reduced thickness is particularly desirable when the pad is to be used in the folded form as shown in FIG. 7 as the longitudinally extending reduced portion 62 forms a hinge-like readily foldable area as shown in FIG. 7.

Figure 8:
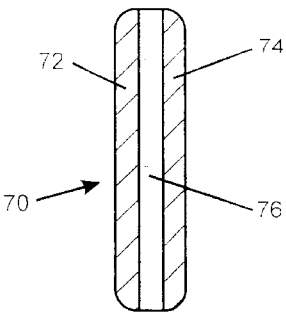
FIG. 8 is a cross sectional view of yet another embodiment of the pad constructed in accordance with this invention.

In FIG. 8 yet another alternative construction of pad is shown. In this embodiment, the pad 70 is composed of two foam layers 72 and 74 or any of the other absorbent materials suggested above, separated by a central layer 76 that may be made of a cotton fabric or any other suitable material. The three layers may be bonded together by a suitable adhesive, or by a thermoforming technique, all of which a re well known in the art. When constructed as suggested in the embodiment of FIG. 8, the pad may also have a reduced central portion and a slitted section to allow the pad to fit over and under scrotum such as shown in the embodiment of FIGS. 1–3 or enlarged central portion as shown in FIG. 9, and/or with the longitudinally extending reduced thickness as suggested in FIGS. 5 and 6 to suit the particular intended application of the article.

Figure 9:
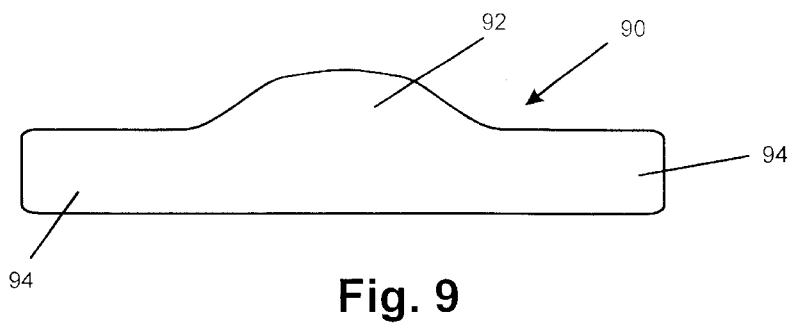
FIG. 9 is a plan view of still another embodiment of pad particularly suitable for use in the stomach crease of an obese person.

In FIG. 9 another embodiment is illustrated, particularly suitable for use by obese people to absorb moisture in and adjacent the stomach crease. In this embodiment, the pad 90 whether made of a single ply of absorbent material or a multiple ply arrangement as shown in FIG. 8, is wider at its mid portion 92 than at its ends 94, as tapering smoothly in a gentle S-curve as shown. The wider mid portion 92 will fit into the deeper portion of the body crease beneath the stomach.

Figure 10:
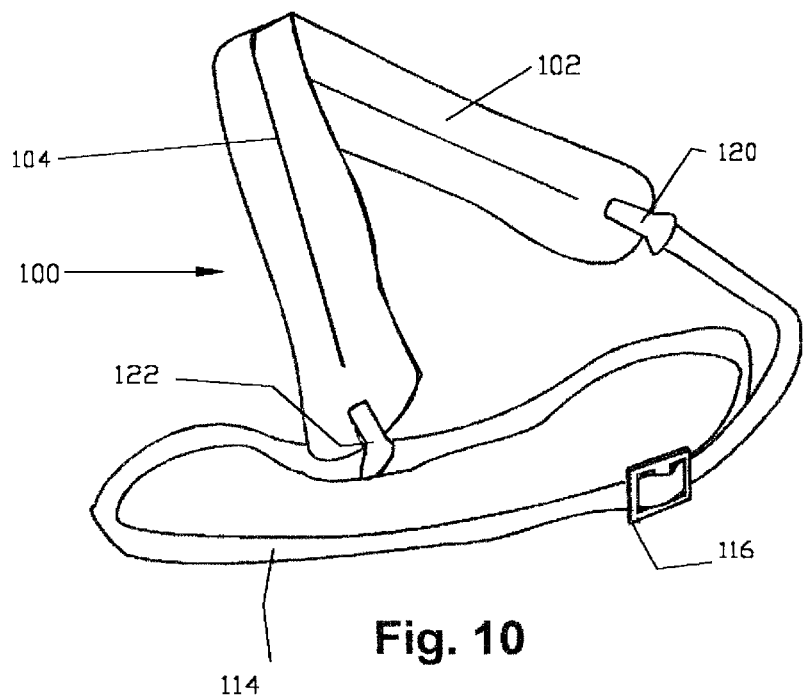
FIG. 10 is a perspective view of an assemby to hold the absorbent article in place.
Figure 11:
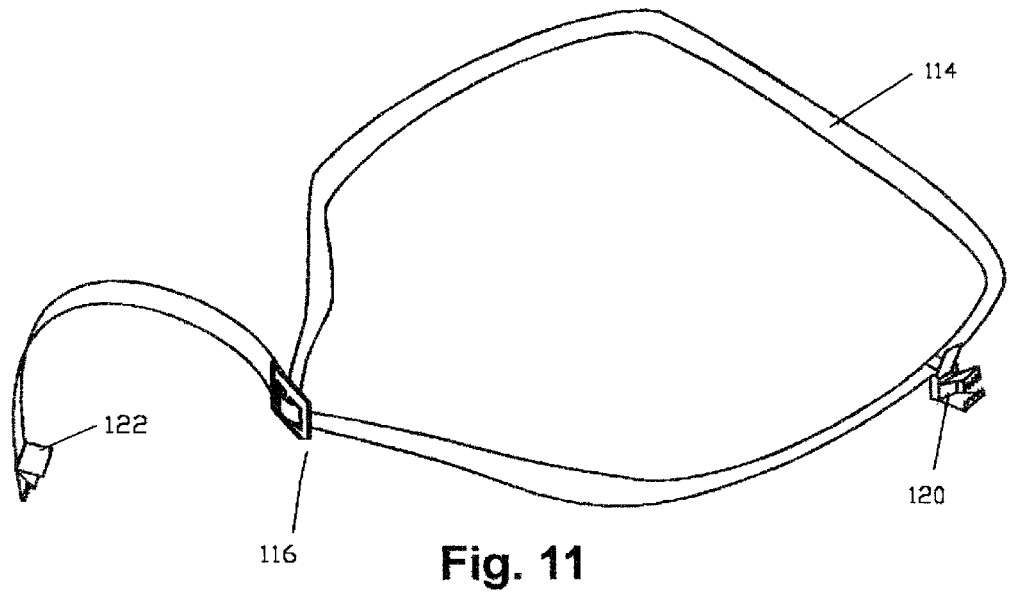
FIG. 11 is a perspective of an elongated belt to hold the absorbent article in place.

In another embodiment shown in FIGS. 10 and 11, an absorbent article 100 includes a body portion 102 having a slit 104 approximately five to eight inches long to allow fitting the pad along the stomach and place the opened section under the scrotum to allow the pad to collect sweat. Alligator clips 120, 122 are used to connect the absorbent article 100 to a belt 114 having a buckle 116.

It should also be appreciated that while an elasticized belt is shown in the embodiment of FIGS. 1 and 4 with alligator-type clips 20 to hold the pad in place, other types of belts and fasteners may be used. It is essential that the method employed for connecting the ends of the belt to the pad be of minimum size and free of sharp corners which would make the article uncomfortable when worn particularly when the wearer is in the sitting position. The invention also contemplates providing thin extensions on the ends of the pad to which the belt may be fastened. The extensions in the form of tabs as suggested at 80 in FIG. 5 may be used to reduce the total thickness of the article at the ends where the attachments of the belt are made. The comfort may also be enhanced by including tabs on each end of the pad designed to lie beneath the clips to prevent them from contacting the skin.

What is claimed is:

1. An absorbent article for use by a male to keep the scrotum dry comprising: an elongated soft pad made of an absorbent material and sized to wrap around the rear of the scrotum and lie against the inner thigh, said pad having opposed ends; a strap connected to the ends of the pad for extending about the waist of the wearer to hold the pad in place about the scrotum and against the inner thigh; and wherein said pad is foldable along a longitudinal center line for providing a portion of the pad on one side of the fold against the thighs and another portion of the pad on the other side of the fold against the scrotum.

2. An absorbent article for use by a male to keep the scrotum dry comprising: an elongated soft pad made of an absorbent material and sized to wrap around the rear of the scrotum and lie against the inner thigh, said pad having opposed ends; a strap connected to the ends of the pad for extending about the waist of the wearer to hold the pad in place about the scrotum and against the inner thigh; and wherein said pad has a narrow central portion intended to engage the rear portion of the scrotum.

3. An absorbent article for use by an obese person to maintain the fat crease at the bottom of the stomach dry comprising: an elongated soft and flexible pad made of an absorbent material and sized to be disposed within the crease about the bottom of the stomach and along the sides thereof; a strap connected to the ends of the pad for extending about the back of the wearer in the region of the waist for holding the pad in place in stomach crease; and wherein said pad is wider at its mid portion than at its end portions.

4. An absorbent article for use by a male to keep the scrotum dry comprising: an elongated soft multilayered pad made of an absorbent material and sized to wrap around the rear of the scrotum and lie against the inner thigh, said pad having opposed ends; a strap connected to the ends of the pad for extending about the waist of the wearer to hold the pad in place about the scrotum and against the inner thigh and wherein said pad has outer layers of absorbent material and an intermediate layer of non stretchable material.

5. An absorbent article for use by an obese person to maintain the fat crease at the bottom of the stomach dry comprising: an elongated soft and flexible pad made of an absorbent material and sized to be disposed within the crease about the bottom of the stomach and along the sides thereof: a strap connected to the ends of the pad for extending about the back of the wearer in the region of the waist for holding the pad in place in stomach crease; and wherein said pad is wider at its mid portion than at its end portions.

6. An absorbent article for use by an obese person to maintain the fat crease at the bottom of the stomach dry comprising: an elongated soft flexible and mutilayered pad mad of an absorbent material and sized to be disposed within the crease about the bottom of the stomach and along the sides thereof: a strap connected to the ends of the pad for extending about the back of the wearer in the region of the waist for holding the pad in place in stomach crease; and wherein said pad has outer layers of absorbent material and an intermediate layer of non stretchable material.

7. An absorbent article for use by a male to keep the scrotum dry comprising: an elongated soft pad made of an absorbent material and sized to wrap around the rear of the scrotum and lie against the inner thigh, said pad having opposed ends; a strap connected to the ends of the pad for extending about the waist of the wearer to hold the pad in place about the scrotum and against the inner thigh; and wherein said absorbent article includes a body portion having a slit to allow fitting the pad along the stomach and allow the pad to collect sweat.

* * * * *